US009642907B2

(12) United States Patent
Ella et al.

(10) Patent No.: US 9,642,907 B2
(45) Date of Patent: May 9, 2017

(54) STABILIZED LIQUID ROTAVIRUS VACCINE COMPOSITION

(75) Inventors: Krishna Murthy Ella, Hyderabad (IN); Victor Jerusha Augustus Harshavardhan Gutla, Hyderabad (IN); Krishna Mohan Vadrevu, Hyderabad (IN); Smita Suneel Singhania, Hyderabad (IN)

(73) Assignee: Bharat Biotech International Limited, Hyderabad (IN)

( * ) Notice: Subject to any disclaimer, the term of this patent is extended or adjusted under 35 U.S.C. 154(b) by 530 days.

(21) Appl. No.: 12/227,250

(22) PCT Filed: May 11, 2007

(86) PCT No.: PCT/IN2007/000190

§ 371 (c)(1),
(2), (4) Date: Jan. 27, 2009

(87) PCT Pub. No.: WO2007/132480

PCT Pub. Date: Nov. 22, 2007

(65) Prior Publication Data

US 2010/0068227 A1 Mar. 18, 2010

(30) Foreign Application Priority Data

May 12, 2006 (IN) ............................. 842/CHE/2006

(51) Int. Cl.

| | |
|---|---|
| ***A61K 39/15*** | (2006.01) |
| ***A61K 39/12*** | (2006.01) |
| ***C12N 7/00*** | (2006.01) |
| *A61K 39/00* | (2006.01) |

(52) U.S. Cl.

CPC .............. *A61K 39/15* (2013.01); *A61K 39/12* (2013.01); *C12N 7/00* (2013.01); *A61K 2039/5254* (2013.01); *A61K 2039/542* (2013.01); *A61K 2039/545* (2013.01); *A61K 2039/55505* (2013.01); *C12N 2720/12334* (2013.01)

(58) Field of Classification Search

None

See application file for complete search history.

(56) References Cited

U.S. PATENT DOCUMENTS

| | | | | |
|---|---|---|---|---|
| 3,629,399 A * | 12/1971 | Mauler et al. | ............. | 424/217.1 |
| 4,205,131 A | 5/1980 | Almeida | | |
| 5,773,009 A | 6/1998 | Glass et al. | | |
| 5,932,223 A * | 8/1999 | Burke et al. | ............... | 424/215.1 |
| 6,210,683 B1 * | 4/2001 | Burke et al. | ............... | 424/230.1 |
| 6,616,931 B1 * | 9/2003 | Burke et al. | ............... | 424/215.1 |
| 2004/0137013 A1 * | 7/2004 | Katinger et al. | ........... | 424/199.1 |
| 2008/0166372 A1 * | 7/2008 | Vande Velde | ............. | 424/205.1 |
| 2009/0035326 A1 * | 2/2009 | Contorni et al. | ........ | 424/196.11 |
| 2009/0238844 A1 * | 9/2009 | Hesse | ........................ | 424/204.1 |
| 2010/0260796 A1 * | 10/2010 | Belin-Poput et al. | ..... | 424/202.1 |

FOREIGN PATENT DOCUMENTS

| | | | |
|---|---|---|---|
| WO | WO 92/01784 | | 2/1992 |
| WO | WO 96/01651 | | 1/1996 |
| WO | WO 99/62500 | | 12/1999 |
| WO | WO 00/56365 | * | 9/2000 |
| WO | WO 02/11540 | | 2/2002 |
| WO | WO 2005/058356 | | 6/2005 |

OTHER PUBLICATIONS

Cunliffe et al., Virus Genes, 1997, 15(1):39-44.*
Sarkar et al., Vaccine, 2003, 21:4728-4735.*
Ferris et al., "Freeze-drying foot-and-mouth disease virus antigens. I. Infectivity studies," Journal of Virological Methods, 1990; 29: 43-52.
Glass et al., "Development of Candidate Rotavirus Vaccines Derived from Neonatal Strains in India," J Infect Dis, Sep. 2005; 192, No. Suppl. 1: S30-S35.
Eagle, "Amino Acid Metabolism in Mammalian Cell Cultures," Science, 1959; 130: 432-437.
Invitrogen: "Basal Medium Eagle (BME) (1X) Liquid," http://www.invitrogen.com/content.cfm?pageID+95&fuseaction=MediaForm.dsp_mediaForm&productId=4, Jan. 21, 2008.
Parashar et al., "Global illness and deaths caused by rotavirus disease in children," Emerg Infect Dis, 2003; 9: 565-72.
World Health Organization (WHO), "Report of the meeting on future directions for rotavirus vaccine research in developing countries," Geneva:WHO, 2000:1-56.
Bresee et al., "The value of surveillance for informing decisions about the introduction of new vaccines," J Infect Dis, 2005; 192: S1-S5.
Glass et al., "Development of candidate rotavirus vaccines derived from neonatal strains in India," J Infect Dis, 2005; 192: S30-S35.
Jagannath et al., "Characterization of human symptomatic rotavirus solates MP409 and MP480 having 'long' RNA electropherotype and subgroup I specificity, highly related to the P6[1], G8 type bovine rotavirus A5, from Mysore, India" Arch. Virology, 2000, 145: 1339-1357.
Lopez et al., "Primary structure of the cleavage site associated with trypsin enhancement of rotavirus SA11 infectivity," Virology, 1985, 144:11-19.

(Continued)

*Primary Examiner* — Nicole Kinsey White
(74) *Attorney, Agent, or Firm* — Seyfarth Shaw LLP

(57) ABSTRACT

The present invention relates to a composition comprising a viral antigen, a first protein and a second protein. Optionally, the composition also comprises three different disaccharaides, or, optionally, the composition comprises a primary sugar and at least one, preferably two secondary sugars. The present invention also relates to the use of a viral antigen, a first protein and a second protein for the manufacture of a composition, preferably a vaccine. The present invention furthermore relates to a method of treatment or prevention of virus associates diseases in humans. Moreover, the present invention relates to a method of adapting a virus to a suitable cell-line. The invention is also useful for the production of virus suspensions suitable for making stable, live/inactivated, monovalent and/or polyvalent, liquid/lyophilized rotavirus vaccine compositions for oral and/or nasal or any other suitable route of administration in human.

6 Claims, 14 Drawing Sheets

(56) References Cited

OTHER PUBLICATIONS

Ericson et al, "Two types of glycoprotein precursors are produced by simian rotavirus SA11. Virology," 1983; 127: 320-332.
Denisova et al., "Rotavirus capsid protein VP5 permeabilizes membranes," Journal of Virology, 1999; 73: 3147-3153.
Gentsch et al., "Identification of group A rotavirus gene 4 type by polymerase chain reaction," J Clin Microbiol, 1992; 30:1365-73.
Gentsch et al., "Similarity of the VP4 protein of human rotavirus strain 116E to that of the bovine B223 strain," Virology, 1993; 194: 424-430.
Scott, et al, "Stability of Pseudorabies virus during freeze drying and storage: Effect of suspending media," Journal of Clinical Microbiolog, Jul. 1976;4: 1-5.

* cited by examiner

Fig. 1: Stability data for Rota virus liquid formulation with different stabilizers after storage at 2-8 °C
Log Titre FFU/0.5 mL
6.8
6.6
6.4
6.2
6
5.8
5.6
5.4
5.2
1
2
3
4
5
6
7
Samples
0 day titer
5week titer
8week titer
12week titer
16week titer
25 week titer
50 week Fig. 2: Stability data for Rota virus liquid formulations with different stabilizers after storage at 25° C
Log Titre FFU/0.5 ml.
7
6
5
4
3
2
1
0
1
2
3
4
5
6
7
Samples
0 Day titer
6 week titer
8 week titer
10 week titer
12 week titer
14 week titer
18 week titer
24 week titer Fig. 3: Stability data for Rota virus liquid formulation with different stabilizers after storage at 37° C
Log Titre FFU/0.5 mL
0
1
2
3
4
5
6
7
1
2
3
4
5
6
7
Samples
0 day titer
3 week titer
6 week titer
8 week titer
10 week titer
12 week titer
14 week titer Fig. 4: Stability data for Rota virus liquid formulations after storage at 2-8° C,25° C and 37° C - Sample 1

Fig. 5: Stability data for Rota virus liquid formulations after storage at 2-8° C,25° C and 37° C - Sample 2

Fig. 6: Stability data for Rota virus liquid formulations after storage at 2-8° C ,25° C and 37° C - Sample 3
Log Titre FFU/0.5 ml
0
1
2
3
4
5
6
7
8
0 day
3 wk
5 wk
6 wk
8 wk
10 wk
12 wk
14 wk
15 wk
16 wk
24 wk
25 wk
Period of Time(weeks)
3 (37C)
3 (25C)
3 (2-8C)

Fig. 7: Stability data for Rota virus liquid formulations after storage at 2-8° C,25° C and 37° C - Sample 4
Log Titre FFU/0.5 mL
7
6
5
4
3
2
1
0
0 day
3 wk
5 wk
6 wk
8 wk
10 wk
12 wk
14 wk
16 wk
24 wk
25 wk
Period of Time (weeks)
4 (37C)
4 (25C)
4 (2-8C)

Fig. 8: Stability data for Rota virus liquid formulations after storage at 2-8° C,25° C and 37° C - Sample 5

Fig. 9: Stability data for Rota virus liquid formulations after storage at 2-8 °C,25° C and 37 °C - Sample 6

Fig. 10: Stability data for Rota virus liquid formulations after storage at 2-8 C,25 C and 37° C - Sample 7

Fig. 11: Stability Data for Rota Virus Lyophilized formulation with stabilizers after storage at different temperature
Log Titre FFU/0.5 ml
7
6
5
4
3
2
1
0
0 day
50 wk at 37° C
50 wk at 25° C
50 wk at 2-8° C
Period of Time
Series1
Series2
Series3
Series4

Fig. 12: Quantitative (Immunoperoxidase Assay) assay of adapted rotavirus harvest at different trypsin concentrations

STABILIZED LIQUID ROTAVIRUS VACCINE COMPOSITION

This application is the United States national stage of International Application No. PCT/IN2007/000190, filed May 11, 2007, which was published under PCT Article 21 in English as International Publication No. WO 2007/132480, and which claims benefit of Indian Patent Application No. 842/CHE/2006 filed May 12, 2006 and the text of application 842/CHE/2006 is incorporated by reference in its entirety herewith.

FIELD OF INVENTION

The present invention relates to a composition comprising a viral antigen, a first protein and a second protein and primary sugar and secondary sugar. The present invention also relates to the use of a viral antigen, a first protein and a second protein for the manufacture of a pharmaceutical composition, preferably a vaccine. The present invention furthermore relates to a method of treatment or prevention of virus associates diseases in humans. Moreover, the present invention relates to a method of adapting a virus to a suitable cell-line.

The invention is also useful for the production of virus suspensions suitable for making stable, live/inactivated, monovalent and/or polyvalent, liquid/lyophilized rotavirus vaccine compositions for oral and/or nasal or any other suitable route of administration in human.

BACKGROUND OF THE INVENTION

Rotavirus infection is the greatest cause of diarrhea related deaths in infants and young children. Every year rotavirus gastroenteritis causes the deaths of 310,000-590,000 infants and young children, worldwide. International health agencies have promoted the development of rotavirus vaccine as the best method for the prevention of morbidity and mortality associated with rotavirus infection. In 1997 and, again, in 2000, the WHO recommended that all new rotavirus vaccines should be tested in Asia and Africa and that this testing should be performed concurrently with trials conducted in the United States and Europe. By doing this safety and efficacy of vaccines might be demonstrated in poor, developing countries early during development, thereby accelerating the availability of new vaccines to the children who are most in need of them.

All rotavirus vaccines developed to date have been based on live rotavirus strains that have been isolated from humans or animals and in vitro reassorted and adapted to cell culture, formulated for oral delivery. Both monovalent and multivalent animal based strains have demonstrated efficacy as candidate vaccines. RotaShield (Wyeth-Ayerst) was licensed but then was withdrawn.

The human rotavirus strain 116E, natural human-bovine reassortant, naturally attenuated is characterized as a human G9 strain into which a single bovine VP4 gene, homologous to P[11] gene segment is naturally introduced. The I321, strain is characterized as a G10P [11] is composed primarily of bovine genes and has only two gene segments, VP5 and VP7 of human origin. These two rotavirus vaccine strains individually have been prepared as pilot lots of monovalent oral rotavirus vaccine liquid formulations for clinical trials to be conducted in India.

Bharat Biotech International Ltd. (BBIL) obtained the human rotavirus strains, 116E and I321 from National Institute of Health (NIH) under the material transfer agreement with National Institute of Allergy and Infectious Diseases (NIAID), NIH, Bethesda, USA. The complete genomic sequence of rotavirus strains 116E and I321 is reported. The original 116E (G9[P11]) and I321 (G10P[11]) were adapted to grow in cell culture by passages in primary African green monkey kidney (AGMK) cells then in MA104 cell substrate and later in Serially Passaged AGMK (SPAGMK). MA104 and SPAGMK cell substrates are not approved by National Regulatory Authorities (NRA) for commercial vaccine production. Hence it is preferable to adapt 116E and I321 and other rotavirus vaccine strains to approved, certified, licensed and fully characterized cell substrate like Vero cell substrate and/or human diploid cells like MRC-5.

WO 02/11540 describes rotavirus vaccine formulations which include buffering agents appropriate for oral administration of rotavirus vaccines. The formulations disclosed in WO 02/11540 also include compounds to stabilize the vaccine compositions against potency loss. More specifically, the compositions disclosed in WO 02/11540 comprise a sugar, phosphate and at least one carboxylate. The stabilities achieved with the formulations of WO 02/11540 vary greatly, and especially at temperatures over 20 degrees Celsius appear to show considerable losses in potency. Accordingly, it was an object of the present invention to provide for alternative compositions of a viral antigen, preferably compositions of rotavirus, which show a good stability.

The objects of the present invention are solved by a composition comprising a viral antigen, a first protein different from said viral antigen, said first protein being selected from human serum albumin (HSA) and recombinant human albumin (rHA), a second protein different from said viral antigen, which second protein is at least partially hydrolyzed, said second protein being selected from lactalbumin. The second protein confers enhanced stability to the vaccine formulation than either of the protein alone.

In one embodiment the composition further comprises three different disaccharides, wherein, preferably, said three different disaccharides are selected from sucrose, lactose, maltose, trehalose, cellobiose, gentobiose, melibiose and turanose. Where as sucrose is used as primary sugar and secondary sugar is selected from the combination of sucrose, lactose, maltose and trehalose. The combination of sugars at particular concentrations further confers stability to the vaccine formulation containing protein additives. The term "primary sugar", as used herein, is meant to refer to a sugar that is present in a composition with other sugars, at an amount greater than of any of the other sugars present. Such other sugars are herein also referred to as "secondary sugars". The "primary sugar" may also be referred to herein as "bulk sugar".

In one embodiment said second protein which is at least partially hydrolyzed is selected from lactalbumin hydrolyzate, yeast hydrolyzate, peptone, and gelatin hydrolyzate.

In one embodiment said first protein is present in the formulation in an amount in the range of from 0.1% (w/v) to 2% (w/v), preferably 0.1% (w/v) to 0.45 (w/v) and said second protein which is at least partially hydrolyzed is present in the formulation, as at least partial hydrolyzate, in an amount in the range of from 0.01% (w/v) to 10% (w/v).

Preferably, said three different disaccharides, or said primary sugar and said at least two secondary sugars are one of the following combinations:

a) sucrose, lactose and maltose, b) sucrose, maltose and trehalose, c) sucrose, lactose and trehalose, d) maltose, lactose and trehalose.

Preferably, the amount of said three different disaccharides together in the formulation is from 20% (w/v) to 70% (w/v).

In a preferred embodiment the amount of sucrose, if present, is from 40% (w/v) to 55% (w/v), preferably 50% (w/v), the amount of lactose, if present, is from 0.1% (w/v) to 10.0% (w/v), preferably 0.5% (w/v), the amount of maltose, if present, is from 0.1% (w/v) to 10.0% (w/v), preferably 0.5% (w/v), and the amount of trehalose, if present, is from 0.1% (w/v) to 10.0% (w/v), preferably 0.5% (w/v).

In one embodiment said viral antigen is a live virus, such as a live attenuated virus, wherein, preferably, said live virus is selected from the group comprising rotaviruses.

Preferably, said live virus is a human live virus, such as human rotavirus.

In a particularly preferred embodiment said human rotavirus is rotavirus strain 116E or I321.

In one embodiment, the composition according to the present invention comprises a live rotavirus at a titre in the range of from $10^4$ to $10^7$ FFU/0.5 ml, human serum albumin in the range of from 0.1% (w/v) to 0.45% (w/v), lactalbumin hydrolysate in the range of from 0.01% (w/v) to 10% (w/v), and either a) sucrose at an amount in the range of from 40% to 55% (w/v), and lactose at an amount in the range of from 0.1% to 10.0% (w/v), and maltose at an amount in the range of from 0.1% to 10.0% (w/v), or b) sucrose at an amount in the range of from 40% to 55% (w/v), and maltose at an amount in the range of from 0.1% to 10.0% (w/v), and trehalose at an amount in the range of from 0.1% to 10.0% (w/v).

In one embodiment the composition according to the present invention further comprises a buffer to adjust the pH of said composition to a value in the range of from 6.8 to 7.8, wherein, preferably, said buffer is a phosphate/citrate buffer.

In one embodiment the composition according to the present invention is made up in Eagles Minimum essential medium, wherein, preferably, it is buffered in a phosphate/citrate buffer at a pH between 6.8 and 7.8.

Preferably, said phosphate/citrate buffer is approximately 310 mM phosphate and approximately 100 mM citrate.

In one embodiment the composition according to the present invention is a vaccine.

The preparation of stable vaccine formulation presents significant challenges. The interactions between the incorporated excipients in the vaccine composition determine the formulation stability. Protein and sugar hydrogen bonding need to be dominant to result with stabilization of the vaccine. The effective contacts of sugar and antigenic protein vaccine should be with appropriate ratio to keep the vaccine stable. A critical sugar concentration is required to have number of protein and sugar hydrogen bonding to keep the vaccine stable for a given period of time, at a given temperature. Sugars have the ability to hydrogen bond to phospholipids membrane and proteins by substituting for structural water. The present study provides the stabilizers used to stabilize the live attenuated Rota virus 116 E and I321 against 2-8° C., 25° C. and 37° C. for an extended period of time.

Appropriate combination of the sugars and proteins with the buffering component preserve and allow the survival and activity of the virus on a long storage period. These additives give structural support to the suspended Rota Virus in the liquid state. Trehalose is preferred to use as stabilizer in vaccine formulation, since it stabilizes the protein structure of the virus and restore the potency on long storage. Combination of Sucrose and Maltose makes effective contacts of sugar and protein (vaccine) to keep the vaccine stable. Human serum albumin supported by Lactalbumin hydrolyzate play prominent role in effective contact of sugar and vaccine protein to keep the vaccine stable.

The objects of the present invention are also solved by the use of a viral antigen, a first protein and a second protein, each being as defined above, and, optionally, three different disaccharides, as defined above, for the manufacture of a composition according to the present invention, preferably for the manufacture of a vaccine, for the treatment or prevention of virus associated, preferably rotavirus associated diseases, such as diarrhea and gastroenteritis.

Preferably, said treatment or prevention comprises administering three oral doses of a safe and effective amount of the composition to an infant within 8-20 weeks of age at the time of dose 1.

Preferably, the use according to the present invention is for the prevention of a virus infection, preferably a rotavirus infection and/or rotavirus gastroenteritis in humans.

The objects of the present invention are also solved by a method of treatment or prevention of virus associated, preferably rotavirus associated diseases in humans by administering to a human an effective amount of the composition according to the present invention.

Preferably, the method according to the present invention, comprises administering three oral doses of a safe and effective amount of the composition to an infant within 8-20 weeks of age at the time of dose 1.

In one embodiment the method according to the present invention, for the prevention of a virus infection, preferably a rotavirus infection and/or rotavirus gastroenteritis in humans.

The objects of the present invention are solved by a method of adapting a virus to a suitable cell line, such as Vero cells, comprising serially passaging said virus through cultures of said suitable cell line, each passage occurring in a medium in the presence of calcium chloride and trypsin.

Preferably, said calcium chloride is present in the range of from 0.1 mg/ml to 1 mg/ml, and said trypsin is present in the range of from 0.1 μg/ml to 30 μg/ml.

In one embodiment said serial passages comprise 2-20 passages, preferably 2-5 passages.

Preferably, each passage occurs over a time period in the range of from 24 hours to 10 days.

Preferably, said virus is human rotavirus.

The present inventors have found that by including a first protein selected from human serum albumin, recombinant human albumin and a second protein which is at least partially hydrolyzed, in a pharmaceutical composition, the stability of this composition with respect to its viral potency can be enhanced. Especially at temperatures 25° C. and 37° C., the compositions according to the present invention show an enhanced stability.

The phrase "the second protein is at least partially hydrolyzed", as used herein, is meant to refer to a scenario, in which this second protein has been at least partially been broken down into its respective amino acid building blocks. The aforementioned phrase is therefore also meant to include scenarios, wherein the second protein does not exist as a complete molecule anymore, but only as a collection of fragments thereof. The aforementioned phrase is meant to also include a scenario wherein the second protein is fully hydrolyzed. All these scenarios are also meant to be included by the phrase "protein hydrolyzate", such as "lactalbumin hydrolyzate", which may include a fully hydrolyzed protein, i.e. a protein broken down into its respective amino acids, or a protein partially broken down, such that a collection of peptides and amino acids exist. Such protein hydrolyzates can be easily made by someone skilled in the art, for example by acid hydrolysis, or they can be commercially obtained.

The stabilizing effect achieved by the presence of the first protein and the second protein is optionally enhanced by the presence of a combination of three different disaccharides, or of a combination of a primary sugar and at least two secondary sugars. Preferred combinations are sucrose, lactose and maltose, and sucrose, maltose and trehalose. The compositions according to the present invention may be used as a vaccine for vaccination against virus infection and virus associated diseases. Preferably, these compositions are buffered at an appropriate pH, usually between 6 and 8, preferably between 6.8 and 7.8. For example, in one embodiment, the composition according to the present invention may be formulated in Eagles minimum essential medium. Preferably, this composition is buffered, for example using a phosphate/citrate buffer.

The present inventors have also devised a method of adapting a virus to a suitable cell-line, which method may be for example used with rotavirus. Such method is performed by serially passaging the virus through cell cultures, wherein the passaging occurs in the presence of calcium chloride and trypsin. This allows for an easy way of adapting virus to a given cell line and furthermore enables the production of virus at high titers.

More specifically and by way of example, the present inventors have adapted 116E and I321 rotavirus strains to Vero cells to produce high titer rotavirus harvest and further characterized the adapted 116E and I321 for making stable, live, monovalent, liquid rotavirus vaccine compositions. Prior to vaccination, oral antacid composition of citrate-bicarbonate buffer is given to buffer stomach acidity of the child.

All rotavirus vaccine strains reported till date are either natural, live, human bovine, naturally or artificially attenuated rotavirus strains or genetically engineered human, bovine strains with various combinations of VP4, VP7 and other genes of human, bovine rotavirus strains. The rotavirus strains 116E (G9P[11]) and I321 (G10P[11]) are natural human-bovine reassortant, naturally attenuated and confer substantial level of immunity in infants and young children. Also the ability of 116E strain to replicate in newborns without causing disease in presence of high titers of maternal antibody make it more promising live, naturally attenuated monovalent rotavirus vaccine candidate.

The present invention provides for pharmaceutical compositions of virus, preferably rotavirus, which show high stability and longevity especially at temperatures above 20° C. The present invention also provides a method for adapting rotavirus, e.g. natural human-bovine reassortant, naturally attenuated rotavirus strains 116E (G9P [11]) and I321 (G10P[11]) to suitable cells, e.g. Vero cells. The method include optimized dose of trypsin (0.1 μg/ml to 30 μg/ml) and/or calcium chloride (100 μg/ml to 1000 μg/ml) for virus activation and virus maintenance medium where high titer ($10^4$ to $10^8$ FFU/ml) of virus harvest is within one to ten days. Also use of the adapted strains for making stable, live, monovalent, liquid rotavirus vaccine composition is envisaged. Furthermore, the present invention provides for the use of a viral antigen, a first protein, a second protein and, optionally, a combination of three different disaccharides for the manufacture of a composition according to the present invention for the treatment or prevention of virus associated diseases, preferably rotavirus associated diseases.

Figure 14:
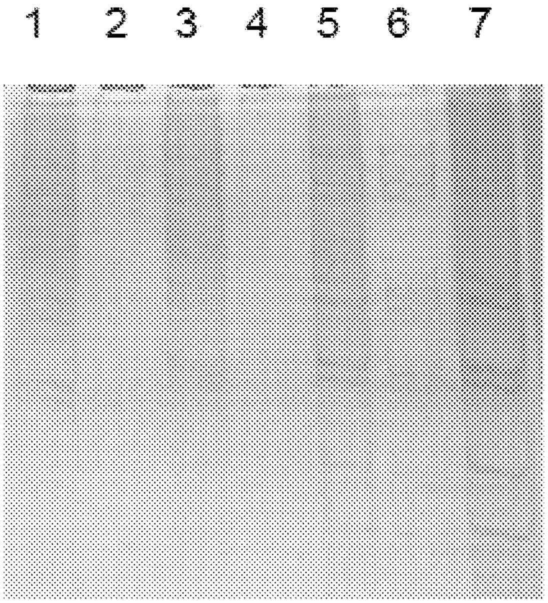

Lane Profile:

1 Rotavirus 116E, SPAGMK Reference
2 Rotavirus 116E, Final lot #61 4004
3 Mix of [Rotavirus 116E, SPAGMK Reference+Rotavirus 116E, Final lot #61 4004]
4 Rotavirus 116E, Final lot #61 4004
5 Rotavirus 116E, SPAGMK Reference
6 Rotavirus 116E, Bulk lot #61BP4004
7 Rotavirus 116E, Working Virus Bank FIG. 14: electropherotyping of Rotavirus I321 on 10% polyacrylamide gel visualized by silver stain.

Lane Profile:

1 Rotavirus I321, SPAGMK Reference
2 Rotavirus I321, Final lot #64 4004
3 Mix of [Rotavirus I321, SPAGMK Reference+Rotavirus I321, Final lot #64 4004]
4 Rotavirus I321, Final lot #64 4004
5 Rotavirus I321, SPAGMK Reference
6 Rotavirus I321, Bulk lot #64BP4004
7 Rotavirus I321, Working Virus Bank

DETAILED DESCRIPTION OF THE INVENTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

The human rotaviruses exhibit a very narrow tissue culture host range. As a consequence, isolation and serial passage of various strains are usually performed in cell cultures such as simian MA-104 or primary monkey kidney (AGMK), both of which are unsuitable for vaccine production. The former cells have not been validated as a substrate for vaccine production and the latter cells are notorious for their contamination with various simian microbial agents including retroviruses.

Many well-characterized rotaviruses have been isolated, serially passaged and triply plaque-purified in commercially available laboratory cell culture systems not suitable for vaccine production. In those instances where it was necessary to use such viruses in vaccine development, the viruses were subsequently passaged and biologically cloned in a cell substrate certified for vaccine development and production. Ideally, virus to be used in vaccines should be isolated and passaged only in tissue culture cells certified to be acceptable for vaccine production. The Vero cell line and MRC-5 cell line meet this requirement because they support efficient growth of rotaviruses.

The present invention relates to compositions comprising a viral antigen and to a method of adaptation of rotavirus human-bovine natural reassortant and naturally attenuated strains 116E (G9P[11]) and I321 (G10P[11]) to Vero cells. The original 116E and I321 rotavirus vaccine strains were adapted to AGMK, MA104 and SPAGMK cell substrate. The SPAGMK is a cell line not approved by National Regulatory Authority (NRA) for commercial production of vaccines. Therefore it was preferable not only to adapt the rotavirus vaccine strains (116E, I321) to FDA or NRA approved cell substrates like Vero cells, human diploid cells, MRC-5 etc. but also to achieve the high titer harvest of the virus within shortest possible duration for commercial production of the rotavirus vaccine. As per data available in scientific literature, several methods for adaptation were studied but were not found satisfactory in terms of virus harvest yield and time period. The novel virus adaptation method in which use of calcium chloride and trypsin at various concentrations for different time periods, for the activation of the virus and in maintenance medium standardized by us was preferred for the mass production of rotavirus vaccine strains. For the oral rotavirus vaccine composition the virus is stabilized in a composition comprising a first protein selected from human serum albumin, recombinant human albumin, bovine serum albumin and porcine serum albumin, and a second protein which is at least partially hydrolyzed, said second protein being selected from human lactalbumin, bovine lactalbumin and porcine lactalbumin. Optionally and preferably, the composition also comprises a combination of three different disaccharides, said three different disaccharides, being selected from sucrose, lactose, maltose, trehalose, cellubiose, gentobiose, melibiose and turanose.

Further components which may be added to the composition include gelatine, gelatine hydrolysate, casitone, D-sorbitol, amino acids, such as alanine, histidine, arginine, glutamine and antibiotics. Before the vaccine administration an antacid composition, e.g. acitrate-bicarbonate buffer is orally administered to buffer stomach acidity, and to ensure delivery of the active vaccine.

According to an embodiment, adaptation of rotavirus vaccine strains 116E and I321 to Vero cell substrate (ATCC Number—CCL-81) for giving high titer virus harvest within ten days was achieved by standardization of calcium chloride concentration ranging from 100 μg/ml to 1000 μg/ml and/or trypsin concentration ranging from 0.1 μg/ml to 30 μg/ml at different time intervals of virus harvest. The virus harvest yield was assessed by ELISA as well as in terms of virus infectivity titers in suitable cell substrate by measuring Focus Forming Units (FFU)/ml.

It is known in the art that rotavirus infectivity is enhanced by trypsin cleavage of VP4 into VP5 and VP8 (7,8). VP5 permeabilizes the host cell membrane for the entry of the rotavirus.

The adapted rotavirus virus, vaccine candidate was further characterized by electropherotyping (FIGS. 13 and 14) and nucleotide sequencing (data not shown).

The antibodies are raised against the rotavirus vaccine strains by following standard protocol for the preparation of immunodiagnostic and immunotherapeutic purposes.

The rotavirus vaccine strains are detected by reverse transcriptase polymerase chain reaction (RT-PCR) wherein the VP4 and VP7 gene and/or VP4 and VP7 gene selectively hybridizing nucleic acid is amplified by using forward and reverse primers for the VP4 gene (Type P11) and/or VP7 gene and a second primer, either within the (G9P [11], G10P [11]) VP4 gene and/or VP7 gene, or located in an adjacent gene.

The following examples are included solely to aid in a more complete understanding of the invention described and claimed herein. The examples do not limit the scope of the claimed invention in any fashion.

Example 1

The original rotavirus vaccine strains 116E (G9P[11]) and I321 (G10P[11]) were supplied by NIAID, NIH, Bethesda, USA to Bharat Biotech International Limited as Vaccine Starting Material strains, were grown in AGMK, MA104 and SPAGMK cell substrate. For the commercial production of rotavirus vaccine these rotavirus strains were adapted to Vero cell substrate and human diploid cells, MRC-5 cell substrate by serial passage of the rotavirus. Calcium chloride concentration ranging from 100 μg/ml to 1000 μg/ml and/or trypsin concentration ranging from 0.1 μg/ml to 30 μg/ml is evaluated for the activation of the rotavirus and in maintenance medium for time periods ranging from 24 hours to 10 days for high titer virus harvest, at each viral passage in the cell substrate. The yield of the virus in cell culture supernatant is assayed by Rotaclone ELISA kit for the detection of the rotavirus antigen on specific antirotavirus antibody precoated ELISA wells.

The infectivity titer of rotavirus pool is titrated in terms of Focus Forming Unit (FFU)/ml by immunoperoxidase Assay In short, the immunoperoxidase assay for rotavirus infectivity titers were estimated by growing confluent layers of MA104 cells in 24 well tissue culture plates. The cells are then washed twice and infected with activated Rotavirus diluted (Log dilutions) suitable and incubated for 12 hours. After incubation the cells were fixed in 3.5% Formalin and probed with Rotavirus antiserum. To this HRPO Conjugated secondary antibody is tagged and stained using AEC Chromogen.

Figure 12:
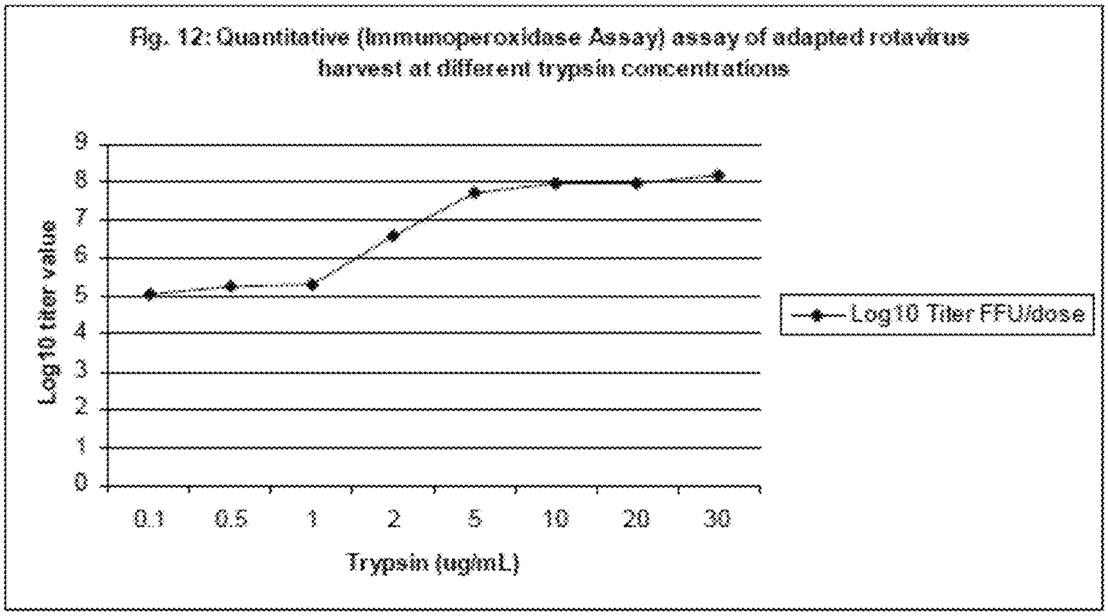
FIG. 12: Quantitative (Immunoperoxidase Assay) assay of adapted rotavirus harvest at different trypsin concentrations

The maximum rotavirus harvest could be achieved, ranging from $10^6$-$18^8$ FFU/ml at various trypsin concentrations within one to ten days (FIG. 12).

Example 2

The rotavirus strains 116E and I321 can be characterized by number of methods, which are known in the art. These include, but are not limited to RT-PCR, RNA hybridization, sequence analysis and genus grouping i.e. RNA electropherotyping. Rotavirus of strains 116E and I321 have distinct RNA/RNA hybrid electrophoresis pattern, compared to other rotavirus strains. They have double-stranded RNA (dsRNA) genome consisting of 11 segments ranging in molecular weight from approximately $2.0\times10^6$ to $0.2\times10^6$ kilo Daltons, out of which VP4 protein is 88,000 Daltons, VP6 is 44,000 Daltons and VP7 is 38000 Daltons. The subtle difference in the mobility of the 11 genomic segments produces a characteristic Electrophoretic band pattern.

Figure 13:
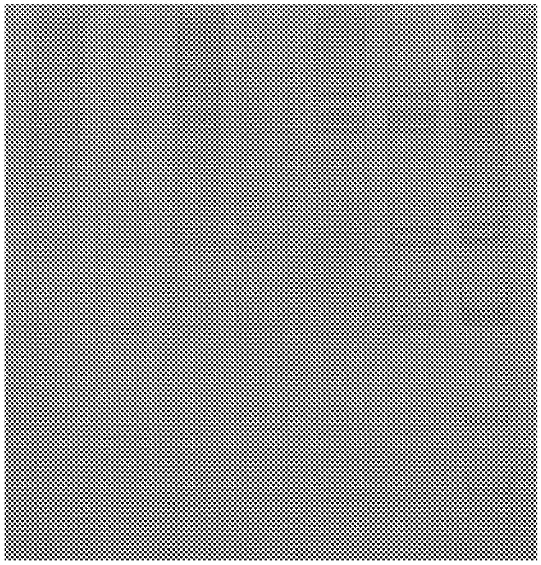
FIG. 13: electropherotyping of 116E RNA on 10% polyacrylamide gel visualized by silver stain.

The electrophoretic band pattern of rotavirus strains 116E and I321 can be checked by isolation of genomic dsRNA by Phenol Chloroform method followed by purification with CC41 anion exchange matrix. The purified dsRNA is electrophoresed on 10% polyacrylamide Gel followed by silver staining for nucleic acids. The 11 segment banding pattern can be compared with the Reference standard of Rotavirus 116E and I321 (FIGS. 13 and 14).

Example 3

The rotavirus strains 116E and I321 can be detected using reverse transcriptase polymerase chain reaction (RT-PCR). Generally, RT-PCR comprises contacting RNA obtaining from a sample containing virus with primers, which selectively hybridizes to the VP4 gene (type P11) and/or VP7 gene (type G9/G10) sequence and synthesizing the first strand of RT-PCR product. A second set of primers, either within the VP4 gene and/or VP7 gene, or located in an adjacent gene would serve as the primer for the second strand synthesis. Primers can have substitutions so long as enough complementary bases exist for selective hybridization.

Example 4

The following non-limiting example is presented to better illustrate the stability of liquid formulation prepared for Live, naturally attenuated oral rotavirus vaccine (116E and/or I321).

Stabilizers are general pharmaceutical excipients and/or specific chemical compounds, which interact and stabilize biological molecules, added to the vaccine and are used in conjunction with lower temperature storage.

The stability of rotavirus at different temperature range 2-8° C., 25° C. and 37° C. were tested in multiple combinations of stabilizer.

Vero Cells infected with rotavirus are harvested, clarified and purified in stabilizers and formulated as liquid preparation. The same lot of rotavirus harvested from infected Vero cells is used in different dose formulations. The liquid preparations of rotavirus vaccines are then incubated at 2-8° C., 25° C. and 37° C. for accelerated stability studies. For real time stability study the liquid preparations of rotavirus vaccines are incubated at 2-8° C. for 12 months. Following these incubations, virus titers were measured by Immunoperoxidase assay.

Figure 1:
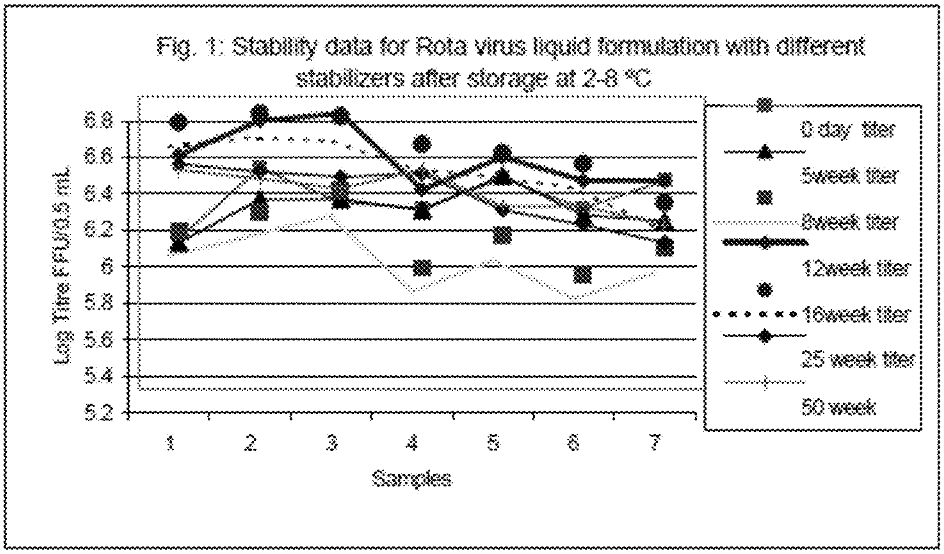
FIG. 1: Stability data for rotavirus liquid formulation with different stabilizers after storage at 2-8° C. for 50 weeks.
Figure 4:
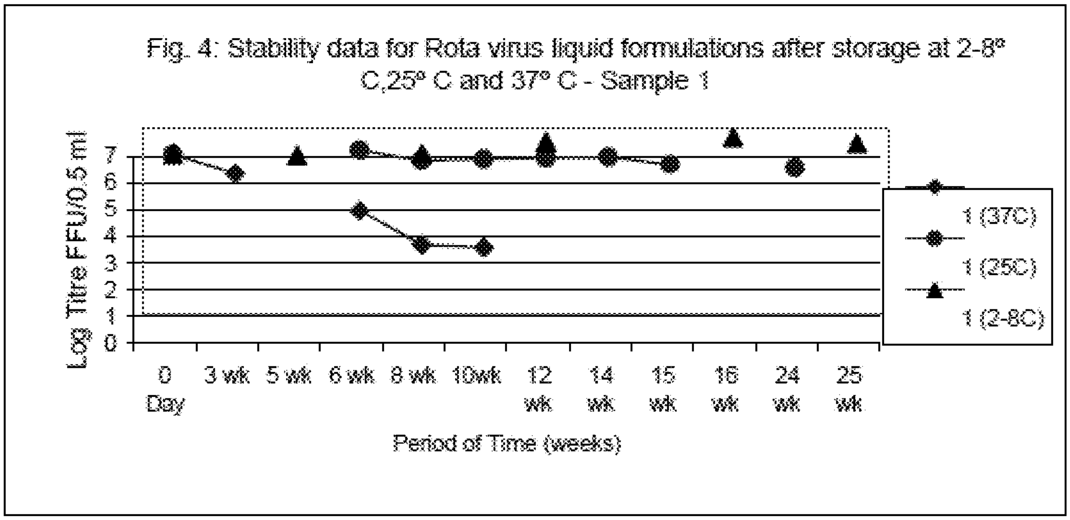
FIG. 4: Stability data for rotavirus liquid formulation after storage at 2-8° C., 25° C. and 37° C. for sample 1.

Moreover, a number of samples were produced to arrive at the composition according to the present invention:

Sample 1 formulated with Eagles Minimum essential medium buffered in 310 mM phosphate and 100 mM citrate containing Sucrose—50%, Lactose—0.5%, Maltose—0.5%, human serum albumin—0.4% and lactalbumin hydrolysate 0.05% at pH 7.4, had 0 day titre of $10^{\wedge 6.02}$ FFU/0.5 ml and at 2-8° C. shows no drop in titre after 50 weeks. (FIGS. 1 & 4)

Figure 2:
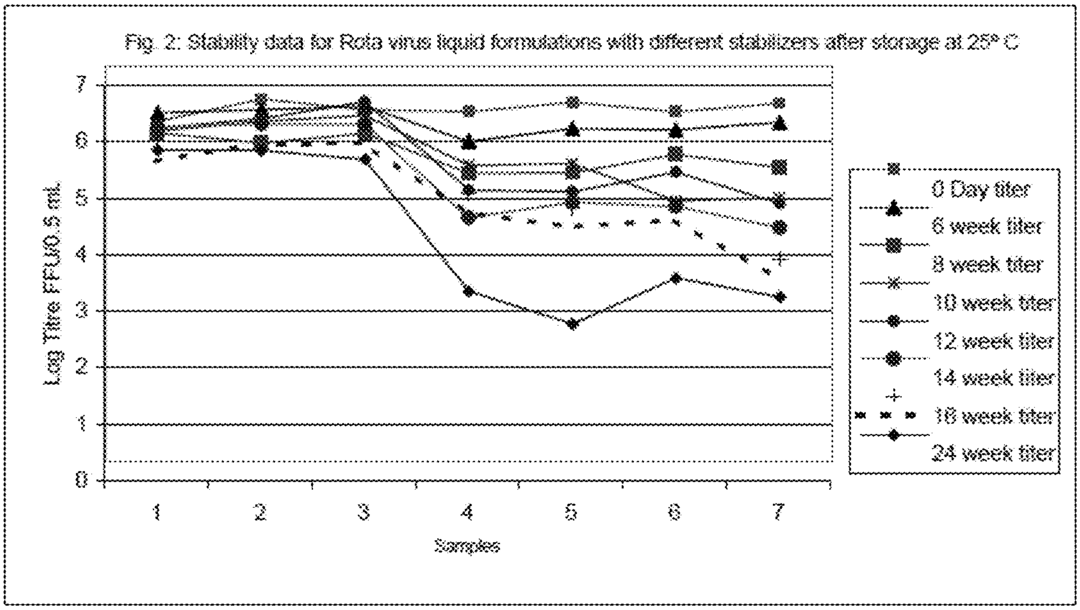
FIG. 2: Stability data for rotavirus liquid formulations with different stabilizers after storage at 25° C.

At 25° C. sample 1 is stable up to 14 wks and there after a drop of 0.5 log titre after 24 weeks is observed. (FIGS. 2 & 4)

Figure 3:
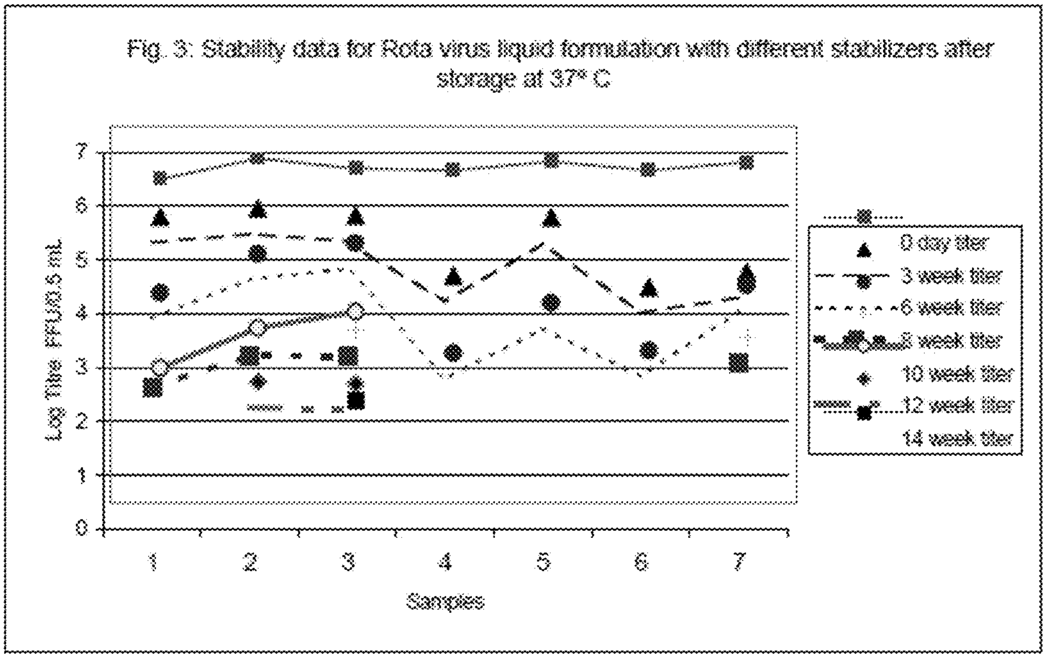
FIG. 3: Stability data for rotavirus liquid formulations with different stabilizers after storage at 37° C.

At 37° C. sample 1 shows a drop in titre is 0.7 log after 3 wks, further 1.41 log drop after 6 wks, and further 1.28 log drop after 8 wks and further 0.11 log drop after 10 wks. (FIGS. 3 & 4)

Figure 5:
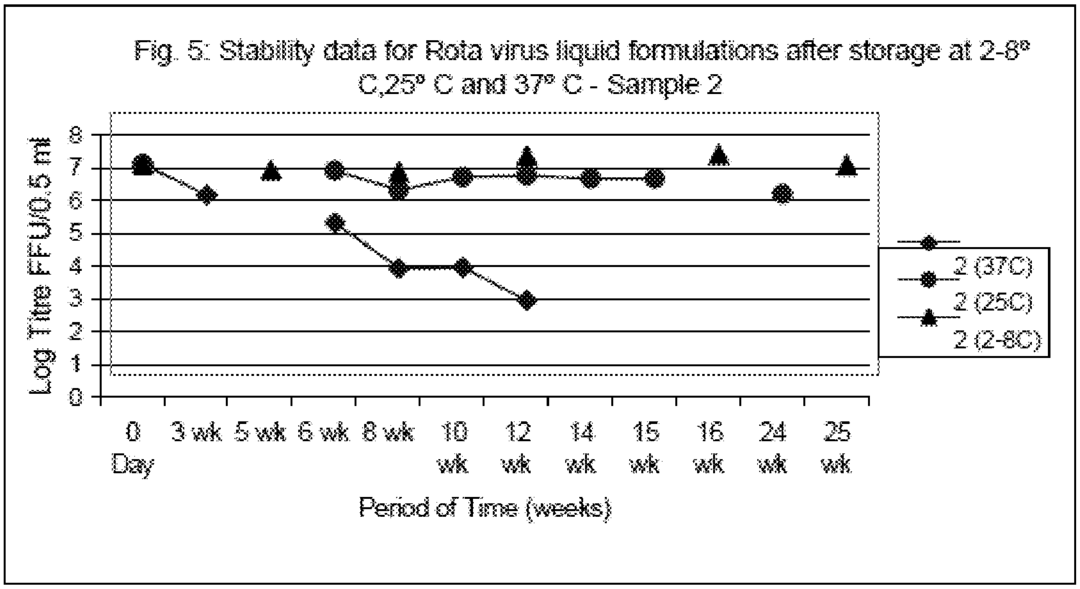
FIG. 5: Stability data for rotavirus liquid formulation after storage at 2-8° C., 25° C. and 37° C. for sample 2.

Sample 2 formulated with Eagles Minimum essential medium buffered in 310 mM phosphate and 100 mM citrate containing Sucrose—50%, Maltose-0.5%, Trehalose—0.5%, human serum albumin—0.4% and lactalbumin hydrolysate 0.05% at pH 7.4, had 0 day titre of $10^{\wedge 6.41}$ FFU/0.5 ml and at 2-8° C. shows 0.06 log drop in titre after 50 weeks. (FIGS. 1 & 5)

At 25° C. sample 2 shows a drop of 0.91 log after 24 weeks. (FIGS. 2 & 5)

At 37° C. Sample 2 shows a drop of 0.94 log after 3 weeks, further 1.78 log drop after 6 weeks, further drop of 3.18 log after 8 weeks, there was no drop in titre from $8^{th}$ week to $10^{th}$ week and further drop of 3.15 log after 10 weeks. (FIGS. 3 & 5)

Figure 6:
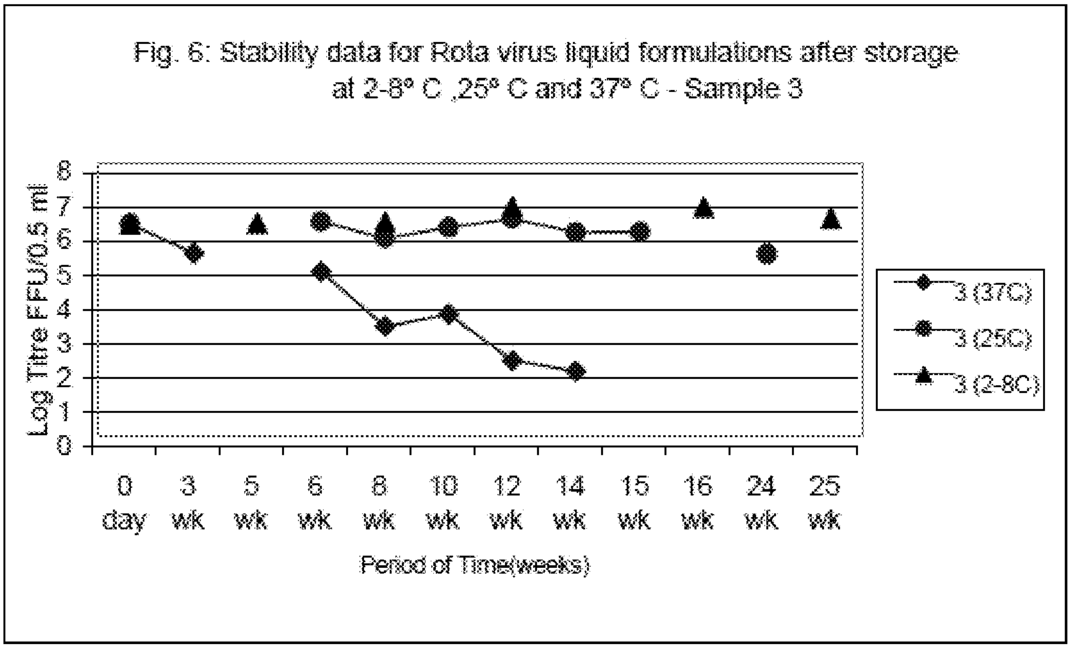
FIG. 6: Stability data for rotavirus liquid formulation after storage at 2-8° C., 25° C. and 37° C. for sample 3.

Sample 3 formulated with Eagles Minimum essential medium buffered in 310 mM phosphate and 100 mM citrate containing Sucrose—50%, Maltose—0.5%, Trehalose—0.95%, human serum albumin—0.4% and lactalbumin hydrolysate 0.05% at pH 7.4, had 0 day titre of $10^{\wedge 6.22}$ FFU/0.5 ml and at 2-8° C. shows no drop in titre after 50 weeks. (FIGS. 1 & 6)

At 25° C. sample 3 shows no drop up to 12 weeks and after 24 weeks shows a drop of 0.88 log in titre. (FIGS. 2 & 6)

At 37° C. sample 3 shows 0.87 log drop after 3 weeks and a further drop of 0.52 log after 6 weeks a further drop of 1.27 log after 10 weeks and a further drop of 1.0 log after 12 weeks and dropped further to 0.3 log after 14 weeks. (FIGS. 3 & 6)

Sample 4 formulated with Eagles Minimum essential medium buffered in 310 mM phosphate and 100 mM citrate containing Sucrose—50%, Maltose—0.5, Lactose—0.5%, human serum albumin 0.4% at pH 7.4, had 0 day titre of $10^{\wedge 6.19}$ FFU/0.5 ml and at 2-8° C. shows no drop in titre after 50 weeks. (FIGS. 1 & 7)

At 25° C. sample 4 shows a drop of 0.53 log titre after 6 weeks and further drop of 0.42 log after 10 weeks and a further drop of 0.05 log titre after 16 weeks and further 1.73 log drop after 24 weeks. (FIGS. 2 & 7)

Figure 7:
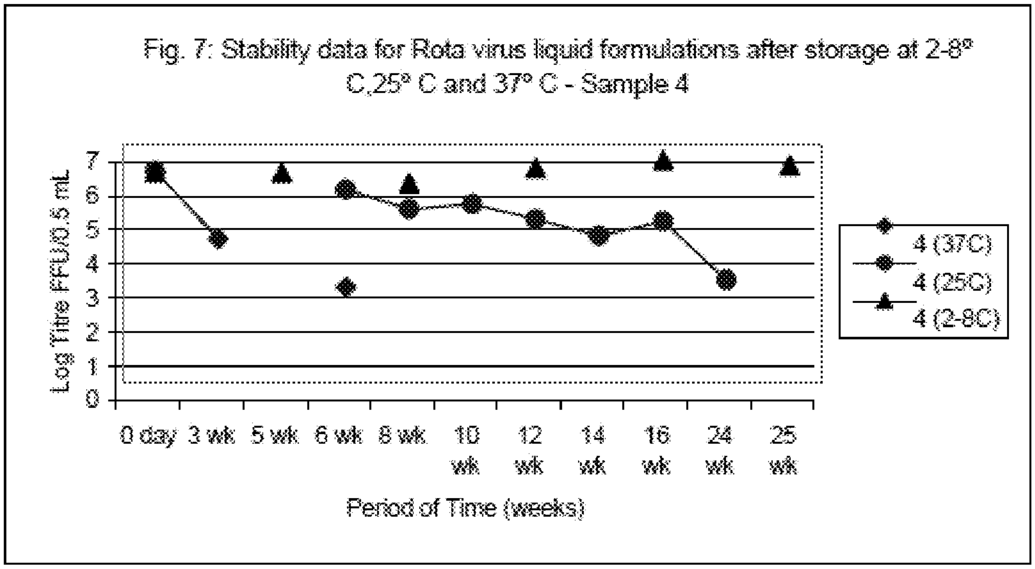
FIG. 7: Stability data for rotavirus liquid formulation after storage at 2-8° C., 25° C. and 37° C. for sample 4.

At 37° C. sample 4 shows a drop of 1.96 log titre after 3 weeks and a further drop of 1.43 log titre after 6 weeks (FIGS. 3 & 7)

Figure 8:
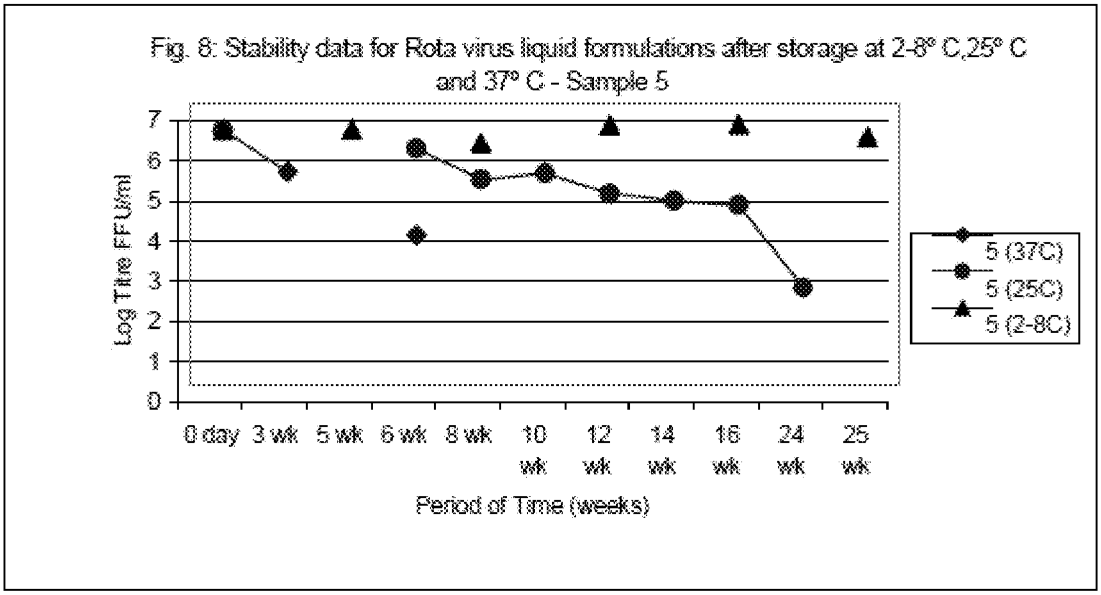
FIG. 8: Stability data for rotavirus liquid formulation after storage at 2-8° C., 25° C. and 37° C. for sample 5.

Sample 5 formulated with Eagles Minimum essential medium buffered in 310 mM phosphate and 100 and mM citrate containing Sucrose—40%, Maltose—5%, and Lactalbumin hydrolysate—1.0% at pH 7.4, had 0 day titre of $10^{\wedge 6.35}$ FFU/0.5 ml and at 2-8° C. shows no drop in titre after 16 weeks and 0.15 log drop after 50 weeks. (FIGS. 1 & 8)

At 25° C. Sample 5 shows a 0.46 log drop in titre from the 0 day titre after 6 weeks. A further drop of 0.62 log titre is observed after 10 weeks. A further drop of 0.78 log in titre is observed after 16 weeks and a further drop of 2.06 log after 24 weeks. (FIGS. 2 & 8)

At 37° C. Sample 5 shows 1.04 log titre drop after 3 weeks from the 0 day titre and further drop of 1.58 log titre after 6 weeks. (FIGS. 3 & 8)

Figure 9:
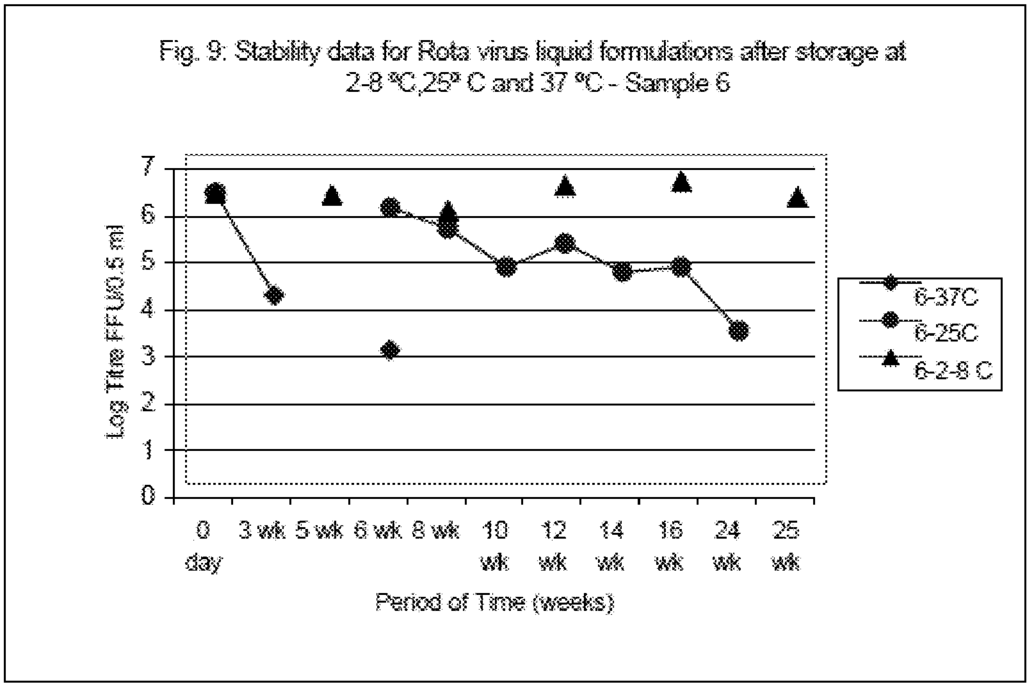
FIG. 9: Stability data for rotavirus liquid formulation after storage at 2-8° C., 25° C. and 37° C. for sample 6

Sample 6 formulated with Eagles Minimum essential medium buffered in 310 mM phosphate and 100 mM citrate containing Sucrose—50%, Maltose—0.5%, Trehalose—0.5%, and human serum albumin 0.4% at pH 7.4, had 0 day titre of $10^{\wedge 6.19}$ FFU/0.5 ml and at 2-8° C. shows no drop in titre after 50 weeks. (FIGS. 1 & 9)

At 25° C. Sample 6 shows a 0.32 log drop in titre from the 0 day titre after 6 weeks. A further drop of 0.46 log titre is observed after 8 weeks. A further drop of 0.82 log in titre is observed after 16 weeks and a further drop of 1.36 log was observed after 24 weeks. (FIGS. 2 & 9)

At 37° C. Sample 6 shows 2.17 log titre drop after 3 weeks from the 0 day titre and further drop of 1.18 log titre after 6 weeks. (FIGS. 3 & 9)

Figure 10:
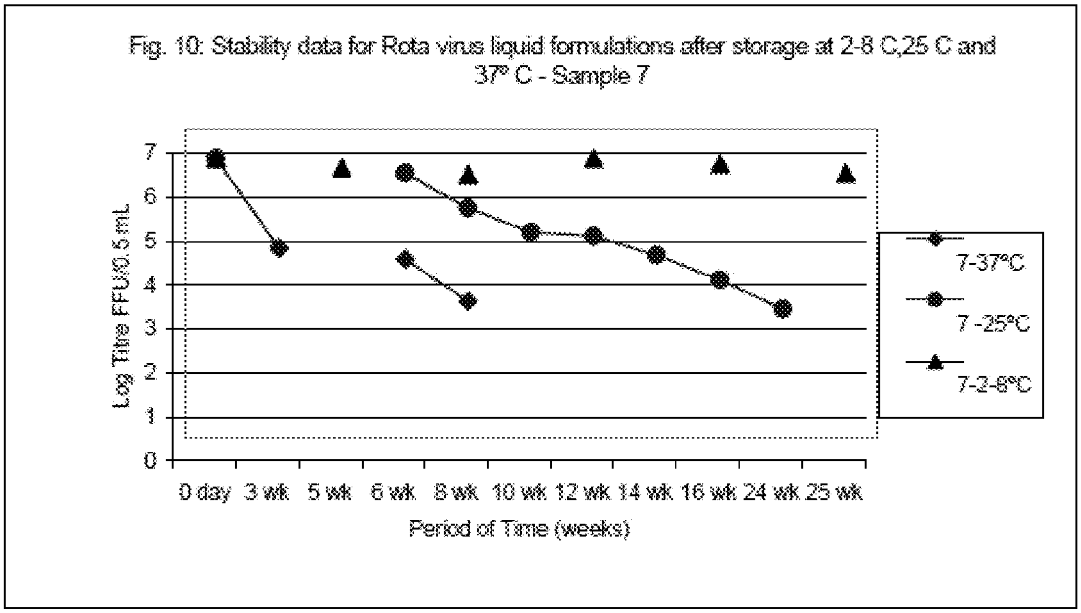
FIG. 10: Stability data for rotavirus liquid formulation after storage at 2-8° C., 25° C. and 37° C. for sample 7.

Sample 7 formulated with Eagles Minimum essential medium buffered in 310 mM phosphate and 100 mM citrate containing Sucrose—50%, Trehalose—0.5%, and Lactalbumin hydrolysate—0.05%, Human Serum Albumin—0.4% at pH 7.4, had 0 day titre of $10^{\wedge 6.34}$ FFU/0.5 ml and at 2-8° C. shows 0.24 log drop in titre after 50 weeks. (FIGS. 1 & 10)

At 25° C. Sample 7 shows a 0.67 log drop in titre from the 0 day titre after 6 weeks. A drop of 3.43 log titre is observed after 24 weeks. (FIGS. 2 & 10)

At 37° C. Sample 7 shows 3.24 log titre drop after 8 weeks from the 0 day titre. (FIGS. 3 & 10)

Figure 11:
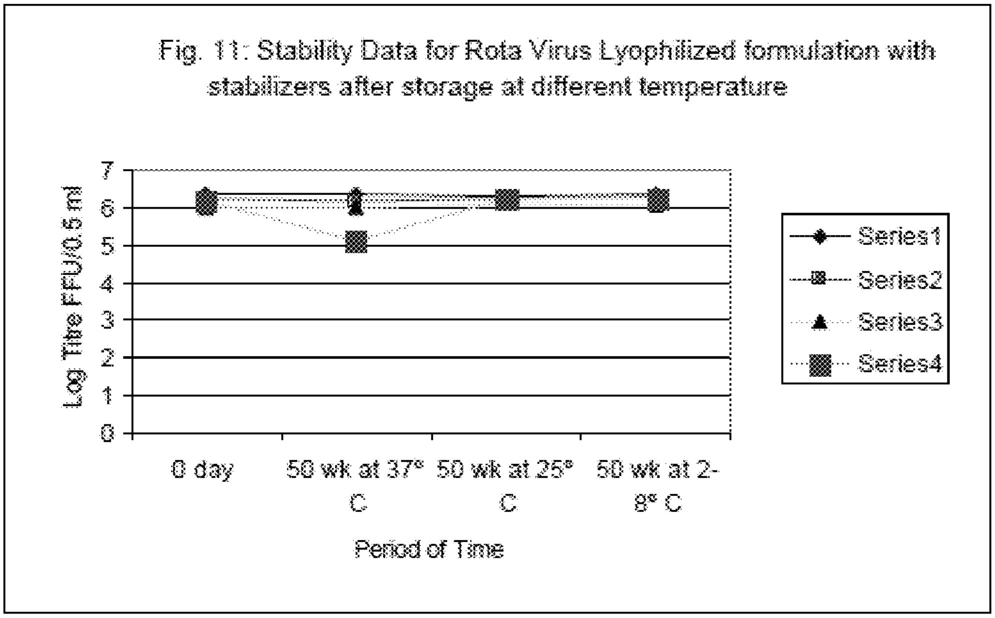
FIG. 11: stability data for rotavirus lyophilized formulation after storage at 2-8° C., 25° C. and 37° C. for 50 weeks, for sample 1-4.

The Lyophilized samples 1-4 are showing stability at 2-8° C., 25° C. and 37° C. up to 50 weeks with out any titre drop (FIG. 11). The stabilizers used are the combinations of 0.1% to 1.0% HAS, 1% SPG (=sucrose phosphate glutamate), 1.2% L-Arginine, 1% D-Sorbitol, 1% Gelatin and 2% Trehalose. (FIG. 11)

It can be seen from FIGS. 1-6 that the samples according to the present invention, namely samples 1-3 show a much better longevity and stability at elevated temperatures above 25° C., especially for longer periods of time.

Hence, particularly preferred combinations in accordance with the present invention include human serum albumin as the first protein, lactalbumin hydrolysate as the second protein, and sucrose, maltose, trehalose, or sucrose, maltose, lactose as the combination of the three different disaccharides.

Example 5

The buffering agent or acid neutralizing agents need to be given orally before administration of oral liquid, live, naturally attenuated rotavirus vaccine formulation to neutralize stomach acidity. The buffering agent is not limited to citrate-bicarbonate buffer, phosphate buffer, succinate, lactate, maleate, fumarate etc.

Acid Neutralizing Buffer Composition (grams/liter): Sodium Citrate 9.6, Sodium Bicarbonate 25.6, pH 6.5 to 8.8

The acid neutralizing capacity (ANC) of the acid-neutralizing buffer can be measured by USP test.

The ANC of citrate-bicarbonate buffer can be 0.35 to 0.50 mEq/ml.

The effect of Citrate Bicarbonate Buffer (CB) on the Infectivity of Monovalent Rotavirus Vaccine in the presence and absence of simulated Gastric Juice (34.8 mEq HCl as simulated Gastric Juice) can be studied.

The rotavirus vaccine formulation along with citrate bicarbonate buffer in presence of 34.8 mEq HCl as simulated Gastric Juices drops 0.1 to 0.2 log rotavirus titer within two hours.

Example 6

For the preparation of lyophilized rotavirus vaccine formulation the rotavirus is stabilized in the stabilizing composition according to the present invention as exemplified in example 4. For lyophilization either the rotavirus bulk is dialyzed into stabilizer for the total removal of tissue culture medium or the rotavirus bulk is diluted 8-15 fold in stabilizer. The formulation has shown good stability studies results.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued The features of the present invention disclosed in the specification, the claims and/or in the accompanying drawings, may, both separately, and in any combination thereof, be material for realising the invention in various forms thereof.

REFERENCES

1. Parashar U D, Hummelman E G, Bresee J S, Miller M A, Glass R I. Global illnesses and deaths caused by rotavirus disease in children. Emerg Infect Dis 2003; 9, 565-72.
2. World Health Organization (WHO). Report of the meeting on future directions for rotavirus vaccine research in developing countries. Geneva:WHO, 2000:1-56.
3. Bresee J S, Hummeman E, Nelson A S, Glass R I. Rotavirus in Asia: The value of surveillance for informing decisions about the introduction of new vaccines. J Infect Dis 2005; 192: S1-S5.
4. Glass R I, Bhan M K, Ray P, Bahal R, Parashar U D, Greenberg H, Rao D C, Bhandari N, Maldonado Y, Ward R L, Bernstein D I, Gentsch J R. Development of candidate rotavirus vaccines derived from neonatal strains in India. J Infect Dis 2005; 192: S30-S35.
5. Glass R I, Gentsch, Bhan M K, Bimal K. Rotavirus strain G9P11. United States Patent, U.S. Pat. No. 5,773,009, Jan. 30, 1998.
6. Jagannath M R, Vethanayagam Reddy B S, Raman S, Rao D. Characterization of human symptomatic rotavirus solates MP409 and MP480 having 'long' RNA electropherotype and subgroup I specificity, highly related to the P6[1], G8 type bovine rotavirus A5, from Mysore, India. Arch. Virology 2000, 145: 1-19.

7. Lopez S, Arias C F, Bell J R, Strauss J H, and Espejo R T. Primary structure of the cleavage site associated with trypsin enhancement of rotavirus SA11 infectivity. Virology 1985, 144:11-19.

8. Ericson B L, Graham D Y, Mason B B and Estes M K. Two types of glycoprotein precursors are produced by simian rotavirus SA11. Virology 1983, 127:320-332.

9. Denisova E, Dowling W, LaMonica R, Shaw R, Scarlata S, Ruggeri F, and Mackow E R. Rotavirus capsid protein VP5 permeabilizes membranes. Journal of Virology 1999, 73:3147-3153.

10. Gentsch J R, Glass R I, Woods P, et. al. Identification of group A rotavirus gene 4 type by polymerase chain reaction. J Clin Microbiol 1992, 30:1365-73.

11. Gentsch J R, Das B K, Jiang B, Bhan M K, and Glass R I. Similarity of the VP4 protein of human rotavirus strain 116E to that of the bovine B223 strain. Virology 1993, 194:424-430.

12. Stability of Pseudorabies virus during freeze drying and storage: Effect of suspending media" Ellen M Scott and W. Woodside. Journal of Clinical Microbiology. July 1976. p 1-5. Vol. 4

We claim:

1. A stabilized liquid rotavirus vaccine composition consisting essentially of:

a live viral antigen rotavirus 116E or I321;

a first protein that is human serum albumin (HSA) at a concentration of 0.1% to 0.45%, wherein the first protein does not include recombinant human albumin;

a second protein which is at least partially hydrolyzed lactalbumin hydrolyzate at a concentration between 0.01% to 0.5%;

a combination of three different disaccharides selected from the group consisting of a first disaccharide combination consisting of one primary sugar sucrose at a concentration of 40% (w/v) to 55% (w/v) and two secondary sugars trehalose and maltose, each secondary sugar is present at a concentration of 0.5% (w/v), and a second disaccharide combination consisting of one primary sugar sucrose at a concentration of 40% (w/v) to 55% (w/v) and two secondary sugars lactose and maltose, each secondary sugar is present at a concentration of 0.5% (w/v); and, a buffer to adjust the pH of said composition to a value between 6.8 and 7.8, wherein the buffer is a phosphate-citrate buffer, wherein the concentration of phosphate is used at 310 mM and the concentration of citrate is used at 100 mM, wherein the buffer does not include succinate and sodium citrate;

wherein said rotavirus is at a titer ranging from $10^4$ to $10^7$ fluorescent focus-forming units (FFU) per 0.5 ml and wherein said vaccine composition may be stored at temperatures ranging from 2° C. to 37° C.

2. The composition according to claim 1, wherein said primary sugar is sucrose present at a concentration of 40% (w/v) to 50% (w/v) and the two secondary sugars of the first disaccharide combination and the second disaccharide combination are present at a concentration of 0.5% (w/v).

3. The composition according to claim 2, wherein the sucrose is present at a concentration of 50% (w/v).

4. The composition according to claim 1, wherein said viral antigen is a live naturally attenuated rotavirus 116E or I321.

5. The composition according to claim 1, wherein said vaccine is stable, in terms of the titer, for at least 3 weeks at 37° C., for at least six months at 25° C., or for at least one year at 2° C. to 8° C.

6. The composition according to claim 1, wherein the rotavirus vaccine composition includes rotavirus activated in a medium containing calcium chloride having a concentration ranging from 100 μg/ml to 1000 μg/ml and trypsin having a concentration ranging from 0.1 μg/ml to 30 μg/ml.

* * * * *